United States Patent
Gruhlke et al.

(10) Patent No.: US 11,659,266 B2
(45) Date of Patent: May 23, 2023

(54) POWER CONTROL BASED AT LEAST IN PART ON USER EYE MOVEMENT

(71) Applicant: QUALCOMM Incorporated, San Diego, CA (US)

(72) Inventors: Russell Gruhlke, San Jose, CA (US); Ravishankar Sivalingam, San Jose, CA (US); Edwin Chongwoo Park, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 265 days.

(21) Appl. No.: 16/949,243

(22) Filed: Oct. 21, 2020

(65) Prior Publication Data
US 2022/0124242 A1 Apr. 21, 2022

(51) Int. Cl.
*H04N 5/232* (2006.01)
*G06T 7/73* (2017.01)
*G06V 40/19* (2022.01)
*G06F 3/01* (2006.01)

(52) U.S. Cl.
CPC ......... *H04N 5/23219* (2013.01); *G06F 3/013* (2013.01); *G06T 7/74* (2017.01); *G06V 40/19* (2022.01); *H04N 5/23241* (2013.01); *G06T 2207/30201* (2013.01)

(58) Field of Classification Search
CPC . G01S 19/14; G02B 27/017; G02B 2027/014; G02B 2027/0187; G06F 3/011; G06F 3/013; G06F 3/0346; G06N 3/08; G06T 19/006

See application file for complete search history.

(56) References Cited

U.S. PATENT DOCUMENTS

2015/0335239 A1* 11/2015 Macfougall ............ A61B 3/113
                                                       351/210
2018/0299953 A1* 10/2018 Selker .................. G02B 27/017
2020/0257358 A1 8/2020 Rosell et al.

FOREIGN PATENT DOCUMENTS

| WO | 2016018487 A2 | 2/2016 |
| WO | 2018191731 A1 | 10/2018 |
| WO | 2020018982 A1 | 1/2020 |

OTHER PUBLICATIONS

International Search Report and Written Opinion—PCT/US2021/071278—ISA/EPO—dated Dec. 9, 2021.

* cited by examiner

*Primary Examiner* — Nelson M Rosario
(74) *Attorney, Agent, or Firm* — Qualcomm Incorporated

(57) ABSTRACT

In some aspects, a user device may receive, from a vision sensor of a user device, first image data associated with a first set of images. The user device may determine, using an image processing model, that a set of images depict a particular type of eye activity of an eye of a user. The user device may cause, based at least in part on determining that the first set of images depict the particular type of eye activity, a power level of a camera of the user device to be reduced.

30 Claims, 9 Drawing Sheets

POWER CONTROL BASED AT LEAST IN PART ON USER EYE MOVEMENT

FIELD OF THE DISCLOSURE

Aspects of the present disclosure generally relate to power control of a user device and, for example, to power control of a device using a low-power sensor to control power according to user eye movement.

BACKGROUND

Sensors are used within user devices for various purposes. Such sensors may be used to sense one or more characteristics associated with a user device. Such characteristics may include one or more characteristics of an environment of the user device and/or biometrics of a user associated with the user device. For example, one or more sensors may be configured to detect whether a user is present, detect activity of the user, detect motion, measure ambient lighting, capture images of the environment, and/or the like.

SUMMARY

In some aspects, a method includes receiving, from a vision sensor of a user device, first image data associated with a first set of images; determining, using an image processing model, that the first set of images depict a first type of eye activity of an eye of a user; causing, based at least in part on determining that the first set of images depict the first type of eye activity, a power level, of a camera of the user device, to be reduced; receiving, from the vision sensor, second image data associated with a second set of images; determining, using the image processing model, that the second set of images depict a second type of eye activity of the eye; and causing, based at least in part on determining that the second set of images depict the second type of eye activity, the power level of the camera to be increased.

In some aspects, a device includes one or more memories and one or more processors, communicatively coupled to the one or more memories, configured to: receive, from a vision sensor of a user device, first image data associated with a first set of images; determine, using an image processing model, that the first set of images depict a first type of eye activity of an eye of a user; cause, based at least in part on determining that the first set of images depict the first type of eye activity, a power level, of a camera of the user device, to be reduced; receive, from the vision sensor, second image data associated with a second set of images; determine, using the image processing model, that the second set of images depict a second type of eye activity of the eye; and cause, based at least in part on determining that the second set of images depict the second type of eye activity, the power level of the camera to be increased.

In some aspects, a non-transitory computer-readable medium storing a set of instructions includes one or more instructions that, when executed by one or more processors of a device, cause the device to: receive, from a vision sensor of a user device, first image data associated with a first set of images; determine, using an image processing model, that the first set of images depict a first type of eye activity of an eye of a user; cause, based at least in part on determining that the first set of images depict the first type of eye activity, a power level, of a camera of the user device, to be reduced; receive, from the vision sensor, second image data associated with a second set of images; determine, using the image processing model, that the second set of images depict a second type of eye activity of the eye; and cause, based at least in part on determining that the second set of images depict the second type of eye activity, the power level of the camera to be increased.

In some aspects, an apparatus includes means for receiving, from a vision sensor of a user device, first image data associated with a first set of images; means for determining, using an image processing model, that the first set of images depict a first type of eye activity of an eye of a user; and means for causing, based at least in part on determining that the first set of images depict the first type of eye activity, a power level, of a camera of the user device, to be reduced.

Aspects generally include a method, apparatus, system, computer program product, non-transitory computer-readable medium, user device, user equipment, wireless communication device, and/or processing system as substantially described with reference to and as illustrated by the drawings and specification.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, both their organization and method of operation, together with associated advantages will be better understood from the following description when considered in connection with the accompanying figures. Each of the figures is provided for the purposes of illustration and description, and not as a definition of the limits of the claims.

BRIEF DESCRIPTION OF THE DRAWINGS

So that the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects. The same reference numbers in different drawings may identify the same or similar elements.

DETAILED DESCRIPTION

Figure 1:
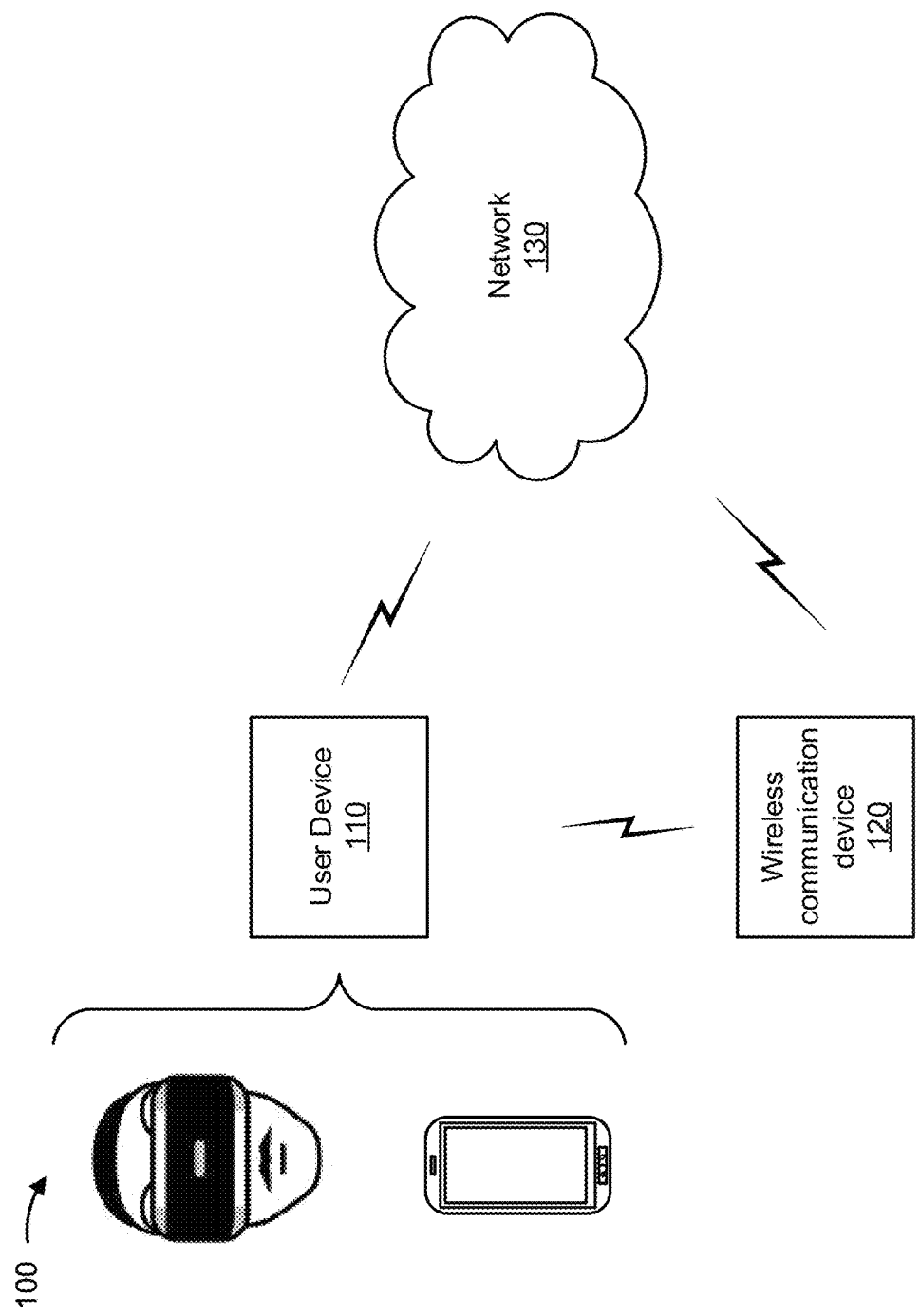
FIG. 1 is a diagram illustrating an example environment associated with power control based at least in part on user eye movement, in accordance with various aspects of the present disclosure.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based at least in part on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

Many user devices (e.g., mobile devices, computers, wearable devices, and/or the like) may include one or more cameras to permit a user to capture images using the user device. Furthermore, in some instances, a camera may be included on a display-side of the user device so that images of a user can be captured while the user is facing and/or interacting with a display of the user device. For example, when being used in connection with a virtual reality (VR) application and/or augmented reality (AR) application, the camera may be used in connection with an always-on motion detection mode to capture images of a user's eyes to determine a gaze direction of the user's eyes, and to control settings of the display according to the gaze direction. For example, the user device may enhance certain portions of images (e.g., increase resolution, brightness, contrast, and/or the like) that are to be presented on an area of the display that is aligned with the gaze direction and/or degrade certain portions of the images that are to be presented, on the display, outside of a range of the gaze direction (e.g., to conserve resources associated with displaying relatively enhanced portions of images that are not being viewed by the user). However, during certain types of eye movement, a user is anatomically incapable of interpreting optics of the eye. For example, during saccades eye movement (e.g., eye movement that occurs when the user is shifting focus from one object to another object, or from one direction to another direction), the user (e.g., the brain of the user) is not interpreting optics from the eyes of the user. Accordingly, during these types of movement, power resources and/or computing resources (e.g., processing resources and/or memory resources) of the user device are being wasted by processing, generating, and/or displaying relatively enhanced images (e.g., images with a relatively higher resolution) on the display of the user device.

Some aspects described herein enable a user device to enter a low-power mode based at least in part on identifying certain types of eye movement of a user. For example, the user device may monitor activity of the eyes of the user, determine that a movement corresponds to a saccades movement (or other type of movement), during which the user is incapable of interpreting optics from the eyes, and cause the camera of the user device to enter a low-power mode and/or the user device to enter a low-power mode. As described herein, the user device may detect the saccades eye movement and reduce the power to a camera (e.g., terminate power to the camera and/or reduce the resolution of the camera). Additionally, or alternatively, the user device may include and/or utilize a vision sensor (e.g., a low-power sensor that consumes less power than a camera of the user device) to monitor and/or track the eye movement of the camera and cause the camera and/or the user device to enter the low-power mode when the low-power sensor detect the saccades eye movement. In this way, when saccades eye movement is detected, the user device can switch to a low-power mode until the saccades eye movement is over. Once the user device detects that the saccades eye movement has ended, the user device may return to the user device and/or the camera to high-power mode to operate in accordance with a desired application of the user device (e.g., a VR application, an AR application, and/or the like).

Accordingly, as described herein, a vision sensor of the user device may be a low-resolution (e.g., less than one megapixel), low-power (e.g., consumes less than 10 mW) sensor that enables always-on motion detection. The vision sensor may be a separate sensor of the camera and/or may correspond to the camera when operating in a low-power mode and/or low-resolution mode, which may consume less power of the user device (e.g., from a battery of the user device) and/or processing resources of the user device. In this way, the vision sensor described herein allows for always-on motion detection (e.g., for eye tracking and/or gaze detection) while consuming less power and/or computing resources than a camera (and/or the camera in a high-power mode).

FIG. 1 is a diagram illustrating an example system 100 in which an image capture module described herein may be implemented, in accordance with various aspects of the present disclosure. As shown in FIG. 1, system 100 may include a user device 110, a wireless communication device 120, and/or a network 130. Devices of system 100 may interconnect via wired connections, wireless connections, or a combination of wired and wireless connections.

User device 110 includes one or more devices capable of including one or more image capture modules described herein. For example, user device 110 may include one or more devices capable of receiving, generating, storing, processing, and/or providing information associated with one or more sensors described herein. Though examples shown in FIG. 1 include a smartphone and a VR device, user device 110 may include any type of communication device and/or computing device, such as a laptop computer, a tablet computer, a handheld computer, a desktop computer, a gaming device, a wearable communication device (e.g., a smart wristwatch, a pair of smart eyeglasses, and/or the like), an AR device, or a similar type of device. As described herein, user device 110 (and/or an image capture module of user device 110) may be used to detect, analyze, and/or perform one or more operations associated with tracking and/or analyzing eye movement of a user.

Similar to user device 110, wireless communication device 120 includes one or more devices capable of receiving, generating, storing, processing, and/or providing information associated with one or more sensors described herein. For example, wireless communication device 120 may include a base station, an access point, and/or the like.

Additionally, or alternatively, similar to user device 110, wireless communication device 120 may include a communication and/or computing device, such as a mobile phone (e.g., a smart phone, a radiotelephone, and/or the like), a laptop computer, a tablet computer, a handheld computer, a desktop computer, a gaming device, a wearable communication device (e.g., a smart wristwatch, a pair of smart eyeglasses, and/or the like), a VR device, an AR device, or a similar type of device.

Network 130 includes one or more wired and/or wireless networks. For example, network 130 may include a cellular network (e.g., a long-term evolution (LTE) network, a code division multiple access (CDMA) network, a 3G network, a 4G network, a 5G network, another type of next generation network, and/or the like), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks. In some aspects, network 130 may include a data network and/or be communicatively with a data platform (e.g., a web-platform, a cloud-based platform, a non-cloud-based platform, and/or the like) that is capable of receiving, generating, processing, and/or providing information associated with an application of the user device 110.

The number and arrangement of devices and networks shown in FIG. 1 are provided as one or more examples. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of system 100 may perform one or more functions described as being performed by another set of devices of system 100.

Figure 2:
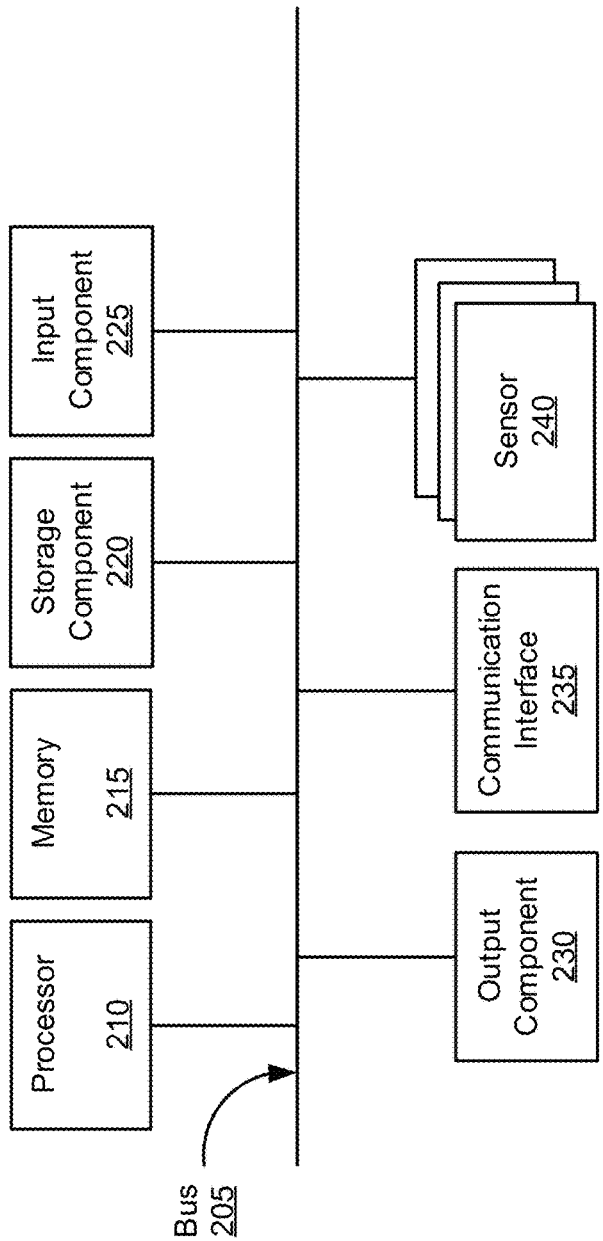
FIG. 2 is a diagram illustrating example components of one or more devices shown in FIG. 1, in accordance with various aspects of the present disclosure.

FIG. 2 is a diagram of example components of a device 200. Device 200 may correspond to user device 110 and/or wireless communication device 120. Additionally, or alternatively, user device 110, and/or wireless communication device 120 may include one or more devices 200 and/or one or more components of device 200. As shown in FIG. 2, device 200 may include a bus 205, a processor 210, a memory 215, a storage component 220, an input component 225, an output component 230, a communication interface 235, and one or more sensors 240 (referred to individually as a "sensor 240" and collectively as "sensors 240").

Bus 205 includes a component that permits communication among the components of device 200. Processor 210 includes a central processing unit (CPU), a graphics processing unit (GPU), an accelerated processing unit (APU), a digital signal processor (DSP), a microprocessor, a microcontroller, a field-programmable gate array (FPGA), an application-specific integrated circuit (ASIC), and/or another type of processing component. Processor 210 is implemented in hardware, firmware, or a combination of hardware and software. In some aspects, processor 210 includes one or more processors capable of being programmed to perform a function.

Memory 215 includes a random-access memory (RAM), a read only memory (ROM), and/or another type of dynamic or static storage device (e.g., a flash memory, a magnetic memory, and/or an optical memory) that stores information and/or instructions for use by processor 210.

Storage component 220 stores information and/or software related to the operation and use of device 200. For example, storage component 220 may include a hard disk (e.g., a magnetic disk, an optical disk, a magneto-optic disk, and/or a solid-state disk), a compact disc (CD), a digital versatile disc (DVD), a floppy disk, a cartridge, a magnetic tape, and/or another type of non-transitory computer-readable medium, along with a corresponding drive.

Input component 225 includes a component that permits device 200 to receive information, such as via user input. For example, input component 225 may be associated with a user interface as described herein (e.g., to permit a user to interact with the one or more features of device 200). Input component 225 may include a touchscreen display, a keyboard, a keypad, a mouse, a button, a switch, a microphone, and/or the like. Additionally, or alternatively, input component 225 may include a sensor for sensing information associated with device 200. More specifically, input component 225 may include a magnetometer (e.g., a Hall effect sensor, an anisotropic magnetoresistive (AMR) sensor, a giant magneto-resistive sensor (GMR), and/or the like), a location sensor (e.g., a global positioning system (GPS) receiver, a local positioning system (LPS) device (e.g., that uses triangulation, multi-lateration, and/or the like), and/or the like), a gyroscope (e.g., a micro-electro-mechanical systems (MEMS) gyroscope or a similar type of device), an accelerometer, a speed sensor, a motion sensor, an infrared sensor, a temperature sensor, a pressure sensor, and/or the like. Output component 230 includes a component that provides output from device 200 (e.g., a display, a speaker, one or more light-emitting diodes (LEDs), and/or the like).

Communication interface 235 includes a transceiver and/or a separate receiver and transmitter that enables device 200 to communicate with other devices, such as via a wired connection, a wireless connection, or a combination of wired and wireless connections. Communication interface 235 may permit device 200 to receive information from another device and/or provide information to another device. For example, communication interface 235 may include an Ethernet interface, an optical interface, a coaxial interface, an infrared interface, a radio frequency (RF) interface, a universal serial bus (USB) interface, a Wi-Fi interface, a cellular network interface, a wireless modem, an inter-integrated circuit ($I^2C$), a serial peripheral interface (SPI), or the like.

Sensor 240 includes one or more devices capable of sensing characteristics associated with an environment of device 200. Sensor 240 may include one or more integrated circuits (e.g., on a packaged silicon die) and/or one or more passive components of one or more flex circuits to enable communication with one or more components of device 200. In some aspects, sensor 240 may include a vision sensor (e.g., an image sensor, an optical sensor, and/or the like), a camera (e.g., a low-resolution camera, a high-resolution camera, and/or the like), and/or the like.

Sensor 240 may include a vision sensor and/or a low-resolution camera (e.g., a video graphics array (VGA)) that is capable of capturing low-resolution images (e.g., images that are less than one megapixel and/or the like). Sensor 240 may be a low-power component or device (e.g., a device that consumes less than 10 milliwatts (mW) of power) that has always-on capability while device 200 is powered on.

Device 200 may perform one or more processes described herein. Device 200 may perform these processes in response to processor 210 executing software instructions stored by a non-transitory computer-readable medium, such as memory 215 and/or storage component 220. "Computer-readable medium" as used herein refers to a non-transitory memory device. A memory device includes memory space within a single physical storage device or memory space spread across multiple physical storage devices.

Software instructions may be read into memory 215 and/or storage component 220 from another computer-readable medium or from another device via communication interface 235. When executed, software instructions stored in memory 215 and/or storage component 220 may cause processor 210 to perform one or more processes described herein. Additionally, or alternatively, hardwired circuitry may be used in place of or in combination with software instructions to perform one or more processes described herein. Thus, aspects described herein are not limited to any specific combination of hardware circuitry and software.

In some aspects, device 200 includes means for performing one or more processes described herein and/or means for performing one or more operations of the processes described herein. For example, the means for performing the processes and/or operations described herein may include bus 205, processor 210, memory 215, storage component 220, input component 225, output component 230, communication interface 235, sensor 240, and/or any combination thereof. More specifically, device 200 includes means for receiving, from a vision sensor, a receiving, from a vision sensor of a user device, first image data associated with a first set of images; means for determining, using an image processing model, that the first set of images depict a first type of eye activity of an eye of a user; means for causing, based at least in part on determining that the first set of images depict the first type of eye activity, a power level, of a camera of the user device, to be reduced; means for receiving, from the vision sensor, second image data associated with a second set of images; means for determining, using the image processing model, that the second set of images depict a second type of eye activity of the eye; and means for causing, based at least in part on determining that the second set of images depict the second type of eye activity, the power level of the camera to be increased.

The number and arrangement of components shown in FIG. 2 are provided as an example. In practice, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
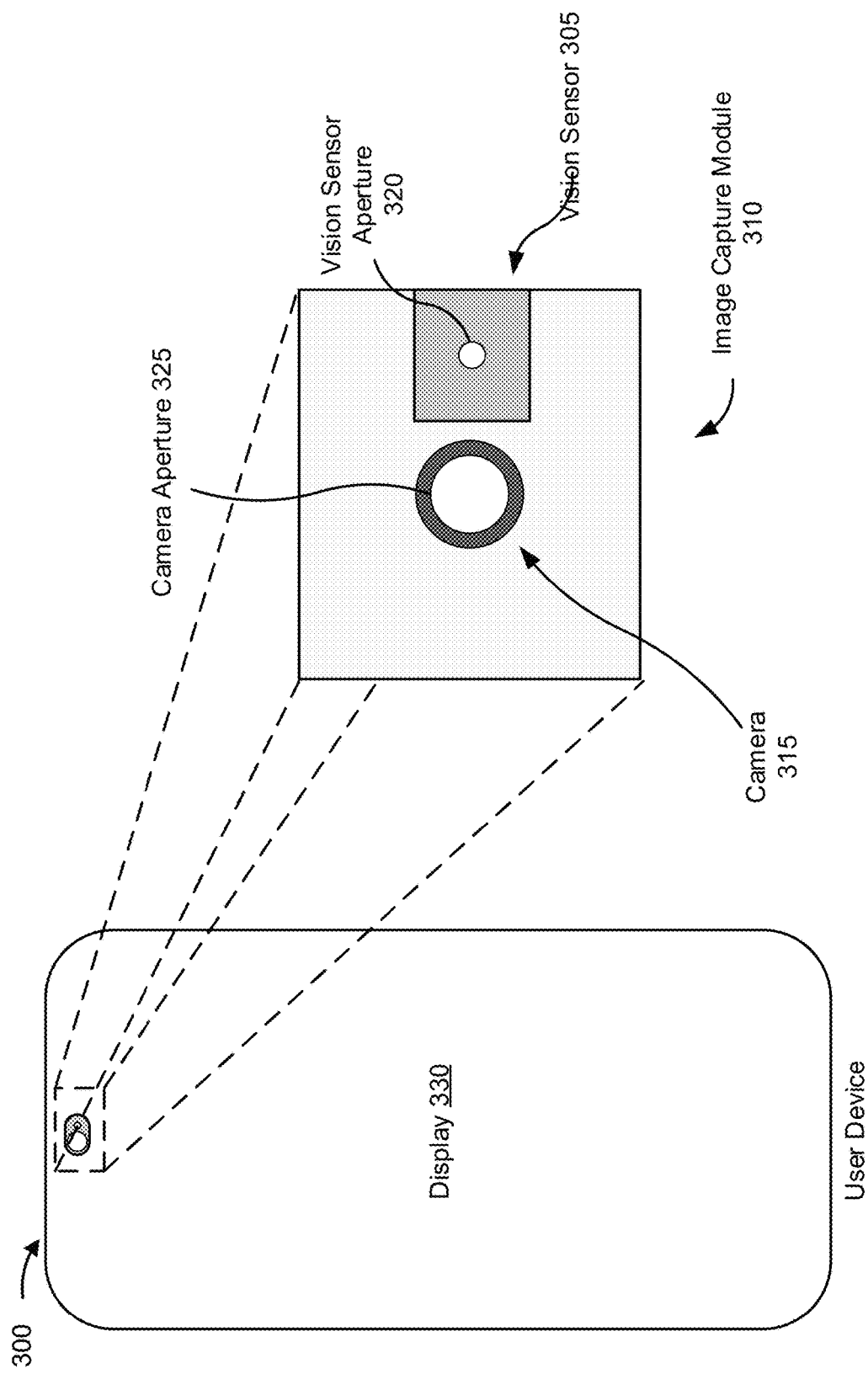
FIG. 3 is a diagram conceptually illustrating an example of a user device that includes a vision sensor, in accordance with various aspects of the present disclosure.

FIG. 3 is a diagram conceptually illustrating an example of a user device 300 that includes a vision sensor 305 in accordance with various aspects of the present disclosure. As shown in the example of FIG. 3, user device 300, which may correspond to user device 110, includes an image capture module 310. Although the image capture module 310 of FIG. 3 includes vision sensor 305 and a camera 315, other configurations of image capture module 310 and/or other configurations of vision sensor 305 and camera 315 are contemplated. For example, vision sensor 305 (which has a vision sensor aperture 320) and camera 315 (which has a camera aperture 325) may be combined or arranged as a single device (e.g., a single camera with a low-power, low-resolution mode and a high-power mode and/or high-resolution mode). In one or more of the following examples, camera 315 may be a high-resolution camera and vision sensor 305 may be a low-power and/or low-resolution camera, as described herein.

Vision sensor 305 may be any suitable sensor that is capable of optically sensing one or more characteristics of an environment of image capture module 310 (which may be the same environment as an environment of user device 300, once installed in the user device). For example, vision sensor 305 may be a low-resolution camera, an optical sensor capable of detecting light (e.g., ambient light, infrared light, an optical communication signal, and/or the like), an infrared sensor, and/or the like.

Vision sensor 305 of image capture module 310 may be a low-power sensor that requires less than 10 mW of power to operate. Vision sensor 305 may require less power than camera 315 of image capture module 310. For example, vision sensor 305 may be a low-resolution camera that requires less than 10 mW (e.g., 1 mW, 2 mW, 5 mW, and/or the like) to capture an image and/or video of the environment via a vision sensor aperture 320. In this way, vision sensor 305 may enable an always-on motion detection capability that enables one or more objects (e.g., an eye of a user) to be detected without the user interacting with a user interface of user device 300, without the user picking up (and/or touching) user device 300, and/or the like. Accordingly, the vision sensor 305 may be in an always-on mode following a start-up operation of the user device, following activation of an always-on mode, and/or the like.

Additionally, or alternatively, vision sensor 305 may include an infrared sensor that facilitates always-on detection when the environment of the image capture module is dark. For example, a device associated with image capture module 310 may include a low-power light emitter that emits infrared light, and vision sensor 305 may sense reflections of the emitted light that can be analyzed (e.g., to detect an eye movement of a user).

As described herein, vision sensor 305 may be configured to have an always-on capability to analyze movement of one or more eyes of a user associated with user device 300 (e.g., a user within a field of view of vision sensor 305). For example, the always-on capability may permit vision sensor 305 to continuously monitor eye movement of the user based at least in part on a particular application (e.g., a VR application, an AR application, and/or other type of image viewing application) of user device 300 being opened and/or activated. For example, the user may open the application to view media (e.g., an image, video, and/or the like), receive a VR experience, receive an AR experience, and/or the like via a display 330 of the user device 300. Accordingly, such always-on capability may facilitate an always-on motion detection capability to identify, track, and/or analyze eye movement of the user, as described herein.

In some aspects, as described herein, based at least in part on detecting certain eye movement (e.g., saccades eye movement) using the always-on capability of vision sensor 305, vision sensor 305 may analyze the eye movement (e.g., a gaze direction, a change in the gaze direction, and/or the like) via an image processing model (e.g., an object processing model, an edge detection model, an optical flow model, and/or the like) and perform one or more actions associated with user device 300 (e.g., cause the camera 315 to enter a low-power mode, cause the camera 315 to enter a low-resolution mode, and/or the like). Further, vision sensor 305, in always-on motion detection mode, may record a sliding window of images captured by vision sensor 305. For example, the sliding window of images may be stored as pre-roll video (e.g., video that is captured in a time period before and/or during detection of an eye and/or certain eye movement). Accordingly, the sliding window of images can be saved as pre-roll video that can be accessed to permit frame-by-frame analysis of the eye and/or movement of the eye in accordance with various aspects of the disclosure.

Camera 315 of user device 300 may be a high-resolution camera that includes a camera aperture 325 and is powered by a power supply (e.g., a battery) when installed within user device 300. As a high-resolution camera, camera 315 may require 100 mW of power or more to capture images and/or video. Camera 315 may be communicatively coupled to a device (e.g., processor 210, input component 225, and/or the like) via a communication bus (e.g., bus 205) to permit camera 315 to be controlled and/or to provide captured images to the device. Although some aspects described herein may describe vision sensor 305 as a separate device from camera 315, vision sensor 305 and camera 315 may be a same device. For example, vision sensor 305 may correspond to camera 315 being in a low-power mode (e.g., that uses a binning technique and/or a skipping technique, among other example techniques that reduce power consumption) and/or a low-resolution mode. In such a case, camera 315 may operate in an always-on detection mode (e.g., an always-on motion detection mode, an always-on gaze detection mode, and/or the like) to detect and/or identify one or more eyes of a user while the user device 300 is displaying, via display 330, media associated with certain applications, as described herein.

In some aspects, image capture module 310 may be formed from and/or configured to include a separable camera module for camera 315 and/or a separable sensor module for vision sensor 305. The sensor module may be attached (e.g., fastened, fixed, connected, glued, and/or the like) to the camera module (e.g., a structure of the camera module) to form image capture module 310. Additionally, or alternatively, the sensor module and the camera module may be attached to a structure of image capture module 310 and/or user device 300 to form image capture module 310. In this way, image capture module 310 may be installed (e.g., prior to installing the display surface) within user device 300 as a single assembled unit or as separable units.

In example 300, image capture module 310 may be installed on a display side of user device 300, referred to herein and shown as display 330. For example, display 330 may permit a user to view media and/or an image being captured (in real-time) by camera 315 (and/or the vision sensor 305). Furthermore, one or more user interfaces (e.g., buttons, touchscreen, and/or the like) may be positioned on the display side to permit the user to control one or more features of camera 315 (e.g., zoom, focus, aspect ratio, resolution, and/or the like). As described herein, the user and/or user device 300 may control camera 315 via an application that is installed on user device 300 and enables control of camera 315. In this way, a field of view of camera 315 and/or vision sensor 305 of FIG. 3 may be directed toward a user handling user device 300 (e.g., via the user holding, gripping, and/or supporting, via a wearable user device support, such as a VR headset, an AR headset, and/or the like). Accordingly, the field of view of camera 315 and/or vision sensor 305 may be configured on user device 300 to permit eye movement of a user that is viewing display 330 to be analyzed in accordance with various aspects of the disclosure.

In this way, the user device may include an image capture module with a camera and a vision sensor with always-on capability to permit the vision sensor to detect and/or analyze eye movement of a user and perform one or more actions associated with the camera and/or the user device.

As indicated above, FIG. 3 is provided as an example. Other examples may differ from what is described above in connection with FIG. 3.

Figure 4A:
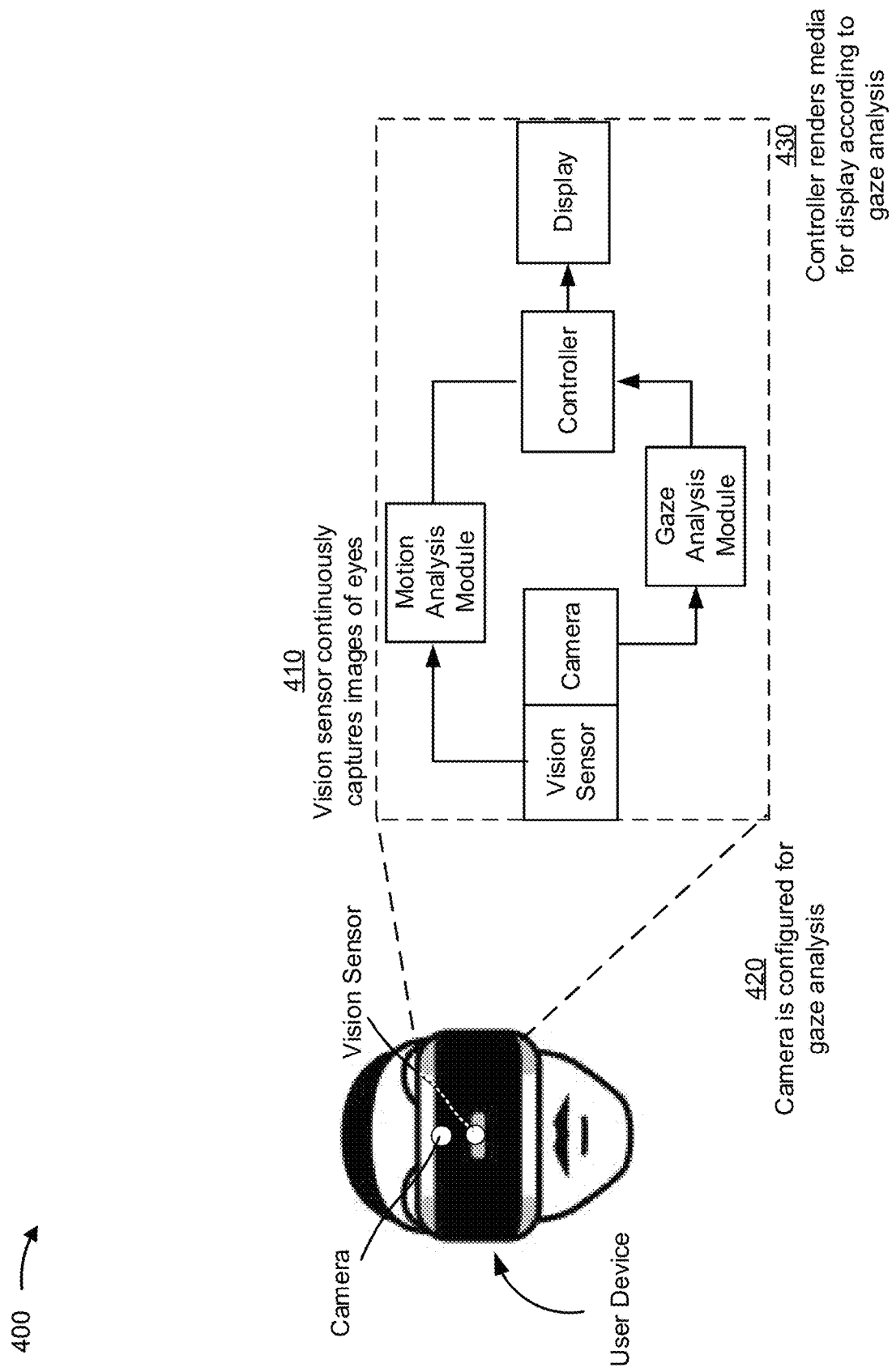
FIGS. 4A-4C are diagrams illustrating examples associated with power control based at least in part on user eye movement, in accordance with various aspects of the present disclosure.
Figure 4B:
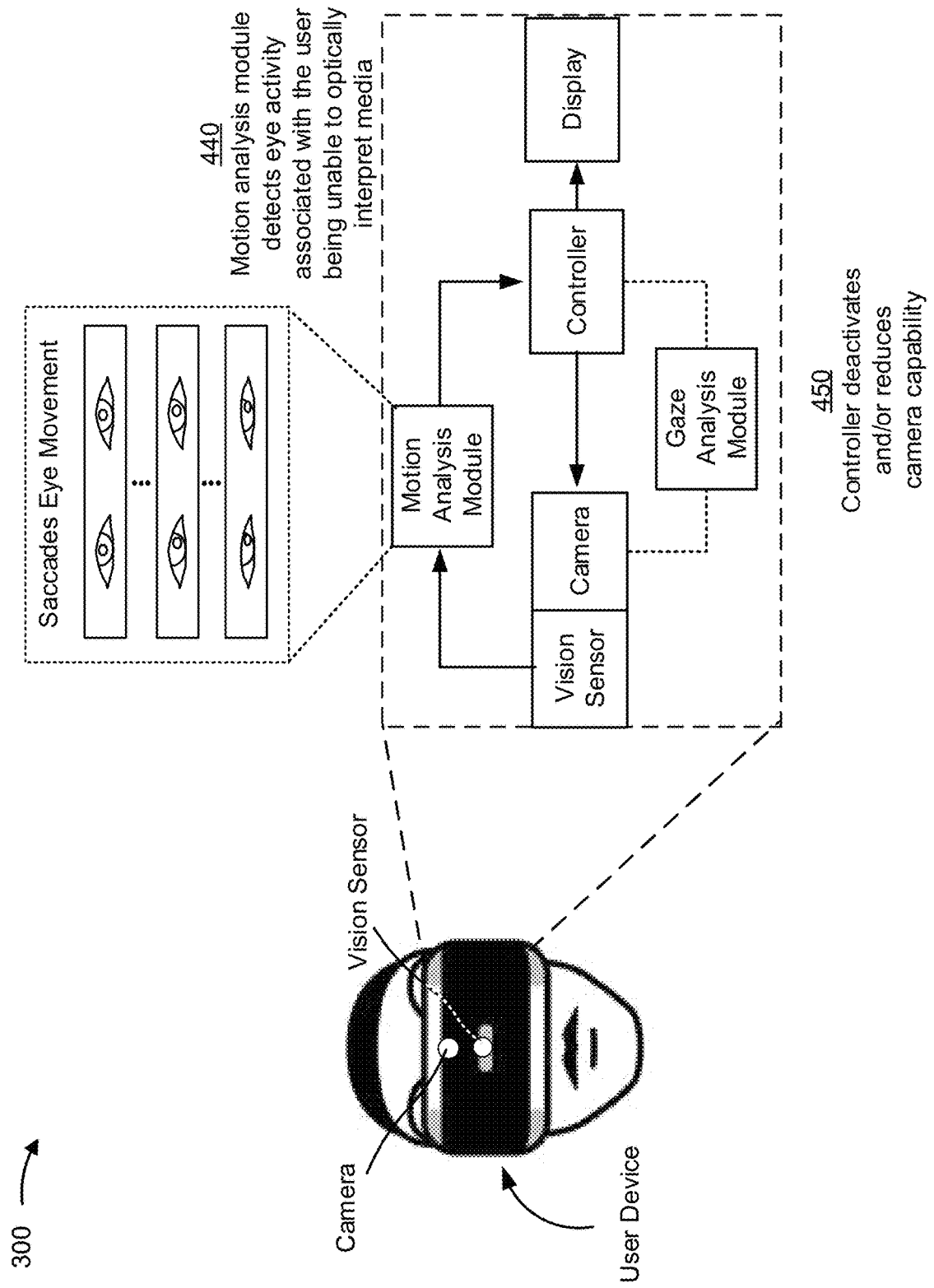
Figure 4C:
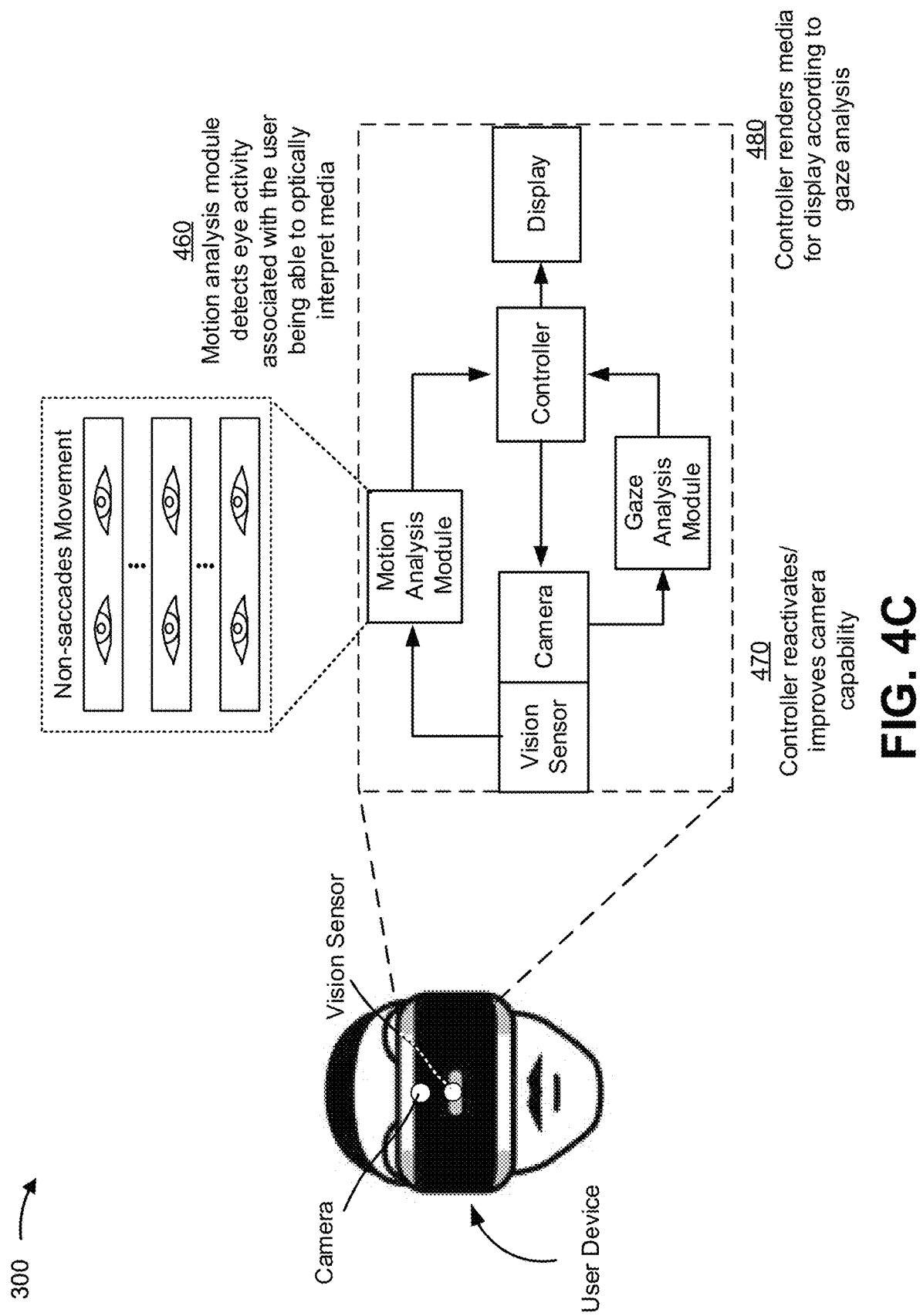

FIGS. 4A-4C are diagrams illustrating examples associated with power control based at least in part on user eye movement, in accordance with various aspects of the present disclosure. As shown in FIGS. 4A-4C, example 400 includes a user device (shown as a VR device and corresponding to user device 300 and/or user device 110) that includes a controller (e.g., processor 210), a vision sensor, and a camera. The user device, as shown, further includes a motion analysis module and gaze analysis module.

While some aspects described herein are described in connection with the vision sensor being a separate device from the camera, the vision sensor and the camera may be a same device. For example, the vision sensor may correspond to the camera when in a low-power mode (e.g., that permits always-on detection capability) and/or a low-resolution mode (e.g., that conserves processing resources).

As shown in FIG. 4A, and by reference number 410, the user device vision sensor continuously captures images of eyes of the user. For example, the vision sensor may be in an always-on mode based at least in part on the user device running an application (e.g., a VR application and/or an AR application) and/or displaying media associated with the application. In this way, the vision sensor may be configured to permit the user device to detect, track, and/or analyze the eyes of the user via the motion analysis module. The motion analysis may be configured to control the controller of the user device according to detected eye movement of the user.

As further shown in FIG. 4A, and by reference number 420, the camera is configured for gaze analysis. For example, the camera may provide, in a high-power mode, images to the controller that can be analyzed to determine a gaze direction of eyes of the user. In the high-power mode the images may have a higher resolution than images captured in a low-power mode of the camera, the images may be provided at a relatively higher frequency than a low-power mode of the camera, among other examples.

As further shown in FIG. 4A, and by reference number 430, the controller renders media for display according to the gaze analysis. For example, the controller may process the high resolution images to the controller to permit the controller to render images on a display of the user device based at least in part on a gaze direction of the eyes of the user. In this way, a user experience (e.g., a VR experience, an AR experience, and/or the like) can be enhanced by enabling the user device to render portions of the images with higher resolution relative to other portions of the display that the user is not viewing.

As shown in FIG. 4B, and by reference number 440, the motion analysis module detects eye activity associated with the user being unable to optically interpret the media on the display of the user device. For example, the motion analysis module may be configured, as described herein, to detect saccades eye movement of the user based at least in part on determining that the eye is moving (or a gaze direction of the eye is changing) at a particular rate that corresponds to the user shifting focus from one object to another. The motion analysis module may utilize any suitable image processing techniques to detect and/or analyze the saccades eye movement and/or other eye movement that indicates that the user is anatomically incapable of interpreting optics during the eye movement.

As further shown in FIG. 4B, and by reference number 450, the controller deactivates the camera and/or reduces a capability of the camera. For example, the controller may shut the camera down and/or reduce an amount of power being supplied to the camera. Additionally, or alternatively, the controller may degrade an image capture setting of the camera (e.g., reduce a resolution of the camera, reduce a frame rate of the camera, and/or the like). Correspondingly, as shown by the dotted lines, the controller may deactivate the gaze analysis module and/or cease to analyze a gaze of the user (e.g., to conserve resources associated with processing any images captured by the camera and/or the vision sensor).

As shown in FIG. 4C, and by reference number 460, the motion analysis module detects eye activity associated with the user being able to optically interpret the media on the display. For example, the motion analysis module may determine that saccades eye movement by the eyes of the user has stopped. In some aspects, the motion analysis module may determine that the saccades eye movement has stopped based at least in part on the eyes not moving (e.g., because the eyes are focused on a particular object being presented on the display). Additionally, or alternatively, the motion analysis module may determine that the saccades eye movement has stopped based at least in part on a rate of movement of the eyes. For example, the motion analysis module may detect that saccades movement has stopped, despite the eye moving, because the eye is moving to track an object of the media moving across an area of the display and/or the eye is slightly moving (or oscillating) in a manner that is representative of a user's focus on an object. In this way, the motion analysis module, via images from the vision sensor, may detect that the saccades eye movement has ended.

As further shown in FIG. 4C, and by reference number 470, the controller reactivates the camera and/or improves a capability of the camera. For example, the controller may provide (or return) power to the camera and/or increase an amount of power being supplied to the camera. Additionally, or alternatively, the controller may improve an image capture setting of the camera (e.g., increase a resolution of the camera, increase a frame rate of the camera, and/or the like). Correspondingly, the controller may activate (or reactivate) the gaze analysis module to analyze a gaze of the user in images captured by the camera (e.g., in a high-power and/or high-resolution mode).

As further shown in FIG. 4C, and by reference number 480, the controller renders the media for display according to the gaze analysis and/or the identified gaze direction of the user, as determined by the gaze analysis module from images of the camera.

In this way, the vision sensor and/or motion analysis module may be utilized to control power of the user device during certain eye movement of a user, thereby conserving power and/or computing resources (e.g., processing resources and/or memory resources) that might otherwise be wasted powering the camera to capture images in a high-power mode and/or processing the images captured in the high-power mode. Such resources would otherwise be wasted because the user is incapable of optically interpreting images being displayed during the certain eye movement.

As indicated above, FIGS. 4A-4C are provided as an example. Other examples may differ from what is described with regard to FIGS. 4A-4C. In practice, there may be additional devices, fewer devices, different devices, or differently arranged devices than those shown in FIGS. 4A-4C. In practice, there may be additional processes, fewer processes, different processes, and/or the processes may be performed in a different order than the examples shown and/or described in connection with FIGS. 4A-4C.

Figure 5:
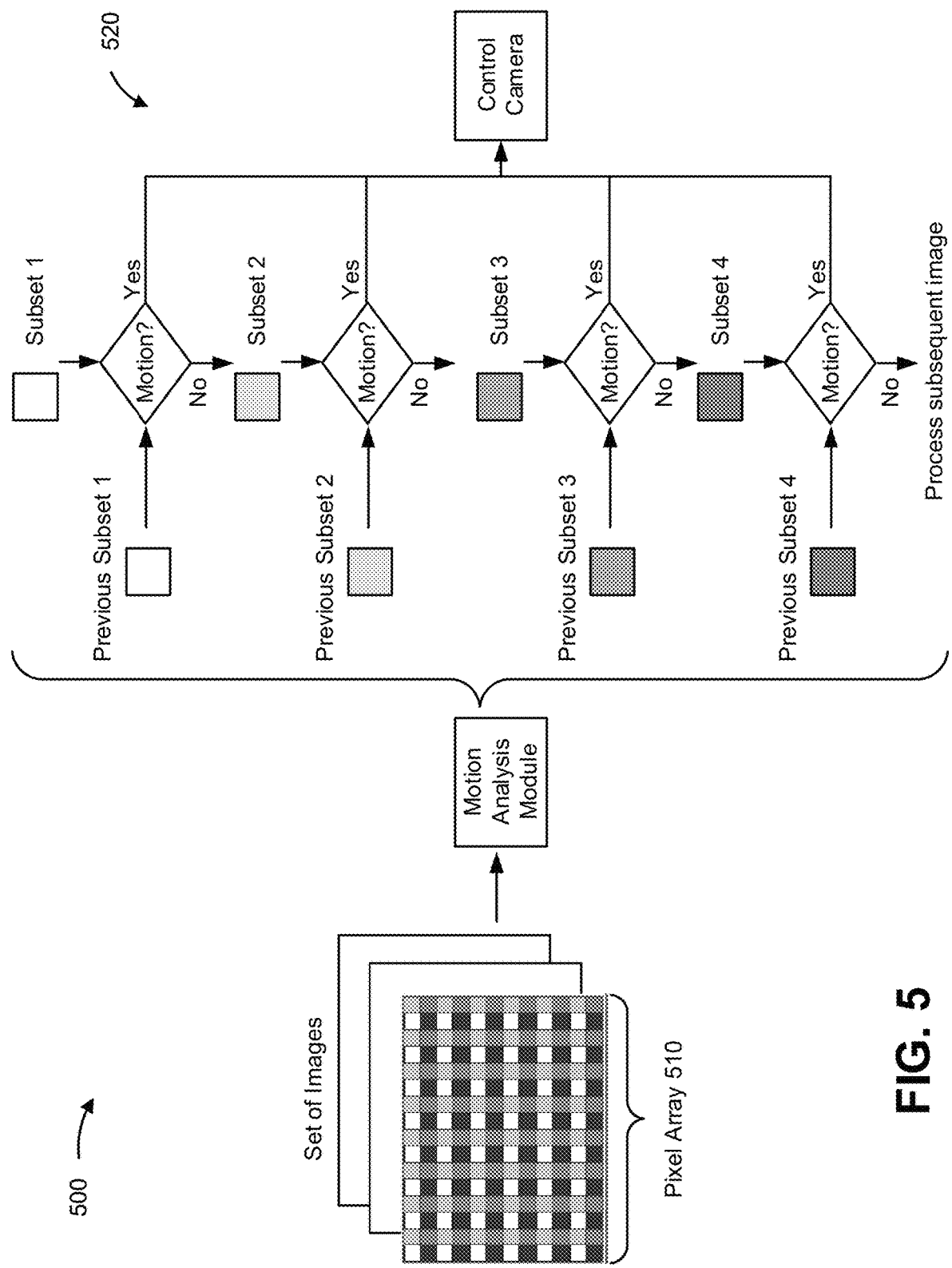
FIG. 5 is a diagram illustrating examples associated with power control based at least in part on user eye movement, in accordance with various aspects of the present disclosure.

FIG. 5 is a diagram of an example 500 associated with power control based at least in part on user eye movement, in accordance with various aspects of the present disclosure.

Example 500 provides an example of a process performed by a motion analysis module (e.g., the motion analysis module of example 400), of analyzing images from a set of images. The set of images has a resolution that is defined by a pixel array 510 (shown as a 16×12 array of pixels). In some aspects, the set of images may depict one or more eyes of a user to permit the motion analysis module to detect motion of the eye and/or a rate of movement of the eye.

As shown in example 500, the pixel array is divided into a subset of pixel arrays (shown as and referred to herein individually as "Subset 1," "Subset 2," "Subset 3," and "Subset 4," and collectively as "the subsets"). Although configurations of the subsets of the pixel arrays in example 500 are shown as being equally distributed pixels, sub-pixel arrays having a same set of dimensions, and/or a sub-pixel arrays having a same quantity of pixels, one or more configurations of the subsets may vary and/or the configurations between the subsets may vary.

As shown by a process 520, the motion analysis module may iteratively analyze a subset of the pixel array of an image relative to a corresponding subset of a pixel array for a previous image of the set of images (shown as and referred to herein as "Previous Subset 1," "Previous Subset 2," "Previous Subset 3," and "Previous Subset 4"). As described herein, relative to coordinates of the set of images, Previous Subset 1 may have a same set of pixel locations as Subset 1, Previous Subset 2 may have a same set of pixel locations as Subset 2, Previous Subset 3 may have a same set of pixel locations as Subset 3, and Previous Subset 4 may have a same set of pixel locations as Subset 4.

In example 500, the motion analysis module may detect motion based at least in part on one or more pixel values of Subset 1 being different from Previous Subset 1. If the motion analysis module detects motion based at least in part on Subset 1 and Previous Subset 1, the motion analysis module may control a setting of a camera (e.g., the camera of example 400). For example, the motion analysis model may cause a controller to deactivate a camera, reduce power to the camera, and/or reduce an image capture setting of the camera. Additionally, or alternatively, the motion analysis model may forgo processing and/or comparing additional subsets of the image. In this way, the motion analysis module may conserve resources associated with comparing Subset 2 and Previous Subset 2, Subset 3 and Previous Subset 3, and/or Subset 4 and Previous Subset 4 in example 500.

If the motion analysis module does not detect motion based at least in part on Subset 1 and Previous Subset 1, as shown, the motion analysis module may sequentially analyze Subset 2 and Previous Subset 2, Subset 3 and Previous Subset 3 (unless motion is detected in a comparison of Subset 2 and Previous Subset 2), and Subset 4 and Previous Subset 4 (unless motion is detected in a comparison of Subset 3 and Previous Subset 3). If motion is not detected based at least in part on subset 4 and Previous Subset 4, the motion analysis module may iteratively perform process 520 on a subsequent image.

In this way, the motion analysis module may iteratively compare similar portions of the images that are a lower resolution than the resolution of the images. Accordingly, the motion analysis module may conserve computing resources by using process 520 to avoid processing every pixel of the set of images.

As indicated above, FIG. 5 is provided as an example. Other examples may differ from what is described with regard to FIG. 5.

Figure 6:
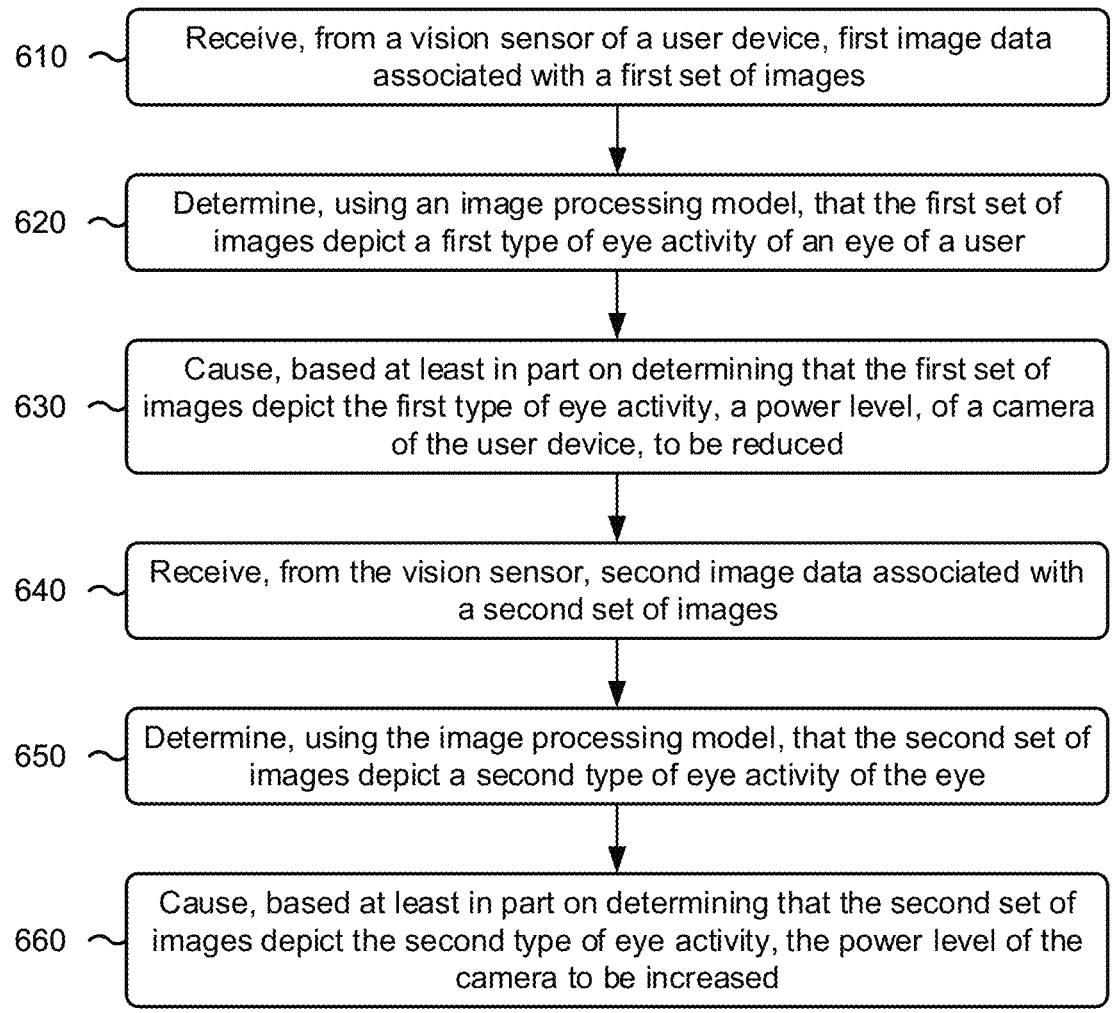
FIGS. 6 and 7 are flowcharts of example processes associated with power control based at least in part on user eye movement, in accordance with various aspects of the present disclosure.

FIG. 6 is a flowchart of an example process 600 associated with power control based at least in part on user eye movement. In some aspects, one or more process blocks of FIG. 6 may be performed by a user device (e.g., user device 110, user device 300, and/or the user device of example 400). Additionally, or alternatively, one or more process blocks of FIG. 6 may be performed by one or more components of device 200, such as processor 210, memory 215, storage component 220, input component 225, output component 230, communication interface 235, and/or sensor 240.

As shown in FIG. 6, process 600 may include receiving, from a vision sensor of a user device, first image data associated with a first set of images (block 610). For example, the user device may receive, from a vision sensor of a user device, first image data associated with a first set of images, as described above.

As further shown in FIG. 6, process 600 may include determining, using an image processing model, that the first set of images depict a first type of eye activity of an eye of a user (block 620). For example, the user device may determine, using an image processing model, that the first set of images depict a first type of eye activity of an eye of a user, as described above.

As further shown in FIG. 6, process 600 may include causing, based at least in part on determining that the first set of images depict the first type of eye activity, a power level, of a camera of the user device, to be reduced (block 630). For example, the user device may cause, based at least in part on determining that the first set of images depict the first type of eye activity, a power level, of a camera of the user device, to be reduced, as described above.

As further shown in FIG. 6, process 600 may include receiving, from the vision sensor, second image data associated with a second set of images (block 640). For example, the user device may receive, from the vision sensor, second image data associated with a second set of images, as described above.

As further shown in FIG. 6, process 600 may include determining, using the image processing model, that the second set of images depict a second type of eye activity of the eye (block 650). For example, the user device may determine, using the image processing model, that the second set of images depict a second type of eye activity of the eye, as described above.

As further shown in FIG. 6, process 600 may include causing, based at least in part on determining that the second set of images depict the second type of eye activity, the power level of the camera to be increased (block 660). For example, the user device may cause, based at least in part on determining that the second set of images depict the second type of eye activity, the power level of the camera to be increased, as described above.

Process 600 may include additional aspects, such as any single aspect or any combination of aspects described below and/or in connection with one or more other processes described elsewhere herein.

In a first aspect, the first type of eye activity corresponds to saccades motion of the eye. In a second aspect, alone or in combination with the first aspect, the first type of eye activity corresponds to eye activity that does not permit the eye to anatomically interpret optics, and the second type of eye activity corresponds to eye activity that permits the eye to anatomically interpret optics.

In a third aspect, alone or in combination with one or more of the first and second aspects, at least one of the first set of images are associated with a larger pixel count than the second set of images, or the first set of images are a higher resolution than the second set of images.

In a fourth aspect, alone or in combination with one or more of the first through third aspects, the vision sensor comprises a low-power sensor that facilitates an always-on motion detection mode to detect at least one of the first type of eye activity or the second type of eye activity. In a fifth aspect, alone or in combination with one or more of the first through fourth aspects, the always-on motion detection mode enables the vision sensor to record a sliding window of images corresponding to the second set of images.

In a sixth aspect, alone or in combination with one or more of the first through fifth aspects, determining that the first set of images depict the first type of eye activity comprises processing a first subset of pixels of an image of the first set of images to determine whether the eye moved relative to a previous image of the first set of images, determining, based at least in part on the first subset of pixels having a different value than corresponding pixels of the previous image, that the eye moved in association with the first type of eye activity, and determining, based at least in part on determining that the eye moved in association with the first type of eye activity, that the first set of images depict the first type of eye activity without processing a second subset of pixels of the image. In a seventh aspect, alone or in combination with one or more of the first through sixth aspects, the second subset of pixels does not include a pixel of the first subset of pixels.

In an eighth aspect, alone or in combination with one or more of the first through seventh aspects, determining that the first set of images depict the first type of eye activity comprises processing a first subset of pixels of an image of the first set of images to determine whether the eye moved relative to a previous image of the first set of images; determining, based at least in part on the first subset of pixels having a same value as corresponding pixels of the previous image, that the eye did not move in association with the first type of eye activity; processing a second subset of pixels of the image of the first set of images to determine whether the eye moved relative to the previous image of the first set of images; determining, based at least in part on the second subset of pixels having a different value than corresponding pixels of the previous image, that the eye moved in association with the first type of eye activity; and determining, based at least in part on determining that the eye moved in association with the first type of eye activity, that the first set of images depict the first type of eye activity. In a ninth aspect, alone or in combination with one or more of the first through eighth aspects, the second subset of pixels does not include a pixel of the first subset of pixels.

In a tenth aspect, alone or in combination with one or more of the first through ninth aspects, the image processing model is configured to detect the first type of eye activity based at least in part on the eye changing a gaze direction and to detect the second type of eye activity based at least in part on the gaze direction of the eye remaining fixed for a threshold time period.

In an eleventh aspect, alone or in combination with one or more of the first through tenth aspects, the camera comprises a high-resolution camera and the vision sensor comprises a low-resolution camera. In a twelfth aspect, alone or in combination with one or more of the first through eleventh aspects, the vision sensor is configured to use less power than the camera.

In a thirteenth aspect, alone or in combination with one or more of the first through twelfth aspects, the vision sensor comprises at least one of the camera in a low-power mode, or the camera in a low-resolution mode. In a fourteenth aspect, alone or in combination with one or more of the first through thirteenth aspects, the camera is configured to capture a third set of images for tracking an eye gaze of the user, wherein a virtual reality rendering or an augmented reality rendering is presented on a display of the user device based at least in part on the tracked eye gaze of the user.

In a fifteenth aspect, alone or in combination with one or more of the first through fourteenth aspects, process 600 includes causing the camera to capture a third set of images, processing the third set of images to track an eye gaze of the eye, and rendering, via a display of a user interface, graphics based at least in part on the eye gaze.

Although FIG. 6 shows example blocks of process 600, in some aspects, process 600 may include additional blocks, fewer blocks, different blocks, or differently arranged blocks than those depicted in FIG. 6. Additionally, or alternatively, two or more of the blocks of process 600 may be performed in parallel.

Figure 7:
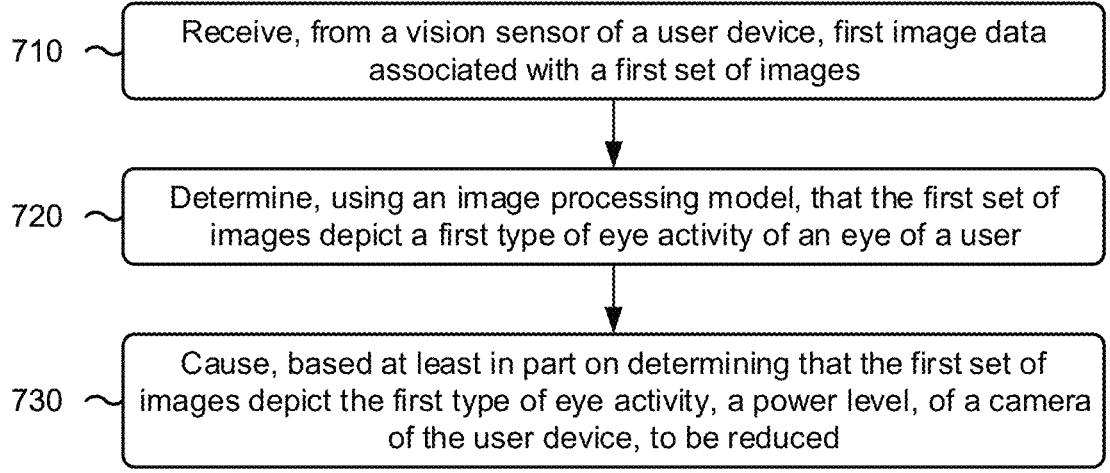

FIG. 7 is a flowchart of an example process 700 associated with power control based at least in part on user eye movement. In some aspects, one or more process blocks of FIG. 7 may be performed by a user device (e.g., user device 110, user device 300, and/or the user device of example 400).

As shown in FIG. 7, process 700 may include receiving, from a vision sensor of a user device, first image data associated with a first set of images (block 710). For example, the user device may receive, from a vision sensor of a user device, first image data associated with a first set of images, as described above.

As further shown in FIG. 7, process 700 may include determining, using an image processing model, that the first set of images depict a first type of eye activity of an eye of a user (block 720). For example, the user device may determine, using an image processing model, that the first set of images depict a first type of eye activity of an eye of a user, as described above.

As further shown in FIG. 7, process 700 may include causing, based at least in part on determining that the first set of images depict the first type of eye activity, a power level, of a camera of the user device, to be reduced (block 730). For example, the user device may cause, based at least in part on determining that the first set of images depict the first type of eye activity, a power level, of a camera of the user device, to be reduced, as described above.

Process 700 may include additional aspects, such as any single aspect or any combination of aspects described below and/or in connection with one or more other processes described elsewhere herein.

In a first aspect, process 700 includes receiving, from the vision sensor, second image data associated with a second set of images; determining, using the image processing model, that the second set of images depict a second type of eye activity of the eye; and causing, based at least in part on determining that the second set of images depict the second type of eye activity, the power level of the camera to be increased.

In a second aspect, alone or in combination with the first aspect, determining that the first set of images depict the first type of eye activity comprises processing a first subset of pixels of an image of the first set of images to determine whether the eye moved relative to a previous image of the first set of images; determining, based at least in part on the first subset of pixels having a different value than corresponding pixels of the previous image, that the eye moved in association with the first type of eye activity; and determining, based at least in part on determining that the eye moved in association with the first type of eye activity, that the first set of images depict the first type of eye activity without processing a second subset of pixels of the image.

In a third aspect, alone or in combination with one or more of the first and second aspects, determining that the first set of images depict the first type of eye activity comprises processing a first subset of pixels of an image of the first set of images to determine whether the eye moved relative to a previous image of the first set of images; determining, based at least in part on the first subset of pixels having a same value as corresponding pixels of the previous image, that the eye did not move in association with the first type of eye activity; processing a second subset of pixels of the image of the first set of images to determine whether the eye moved relative to the previous image of the first set of images; determining, based at least in part on the second subset of pixels having a different value than corresponding pixels of the previous image, that the eye moved in association with the first type of eye activity; and determining, based at least in part on determining that the eye moved in association with the first type of eye activity, that the first set of images depict the first type of eye activity.

Although FIG. 7 shows example blocks of process 700, in some aspects, process 700 may include additional blocks, fewer blocks, different blocks, or differently arranged blocks than those depicted in FIG. 7. Additionally, or alternatively, two or more of the blocks of process 700 may be performed in parallel.

The foregoing disclosure provides illustration and description, but is not intended to be exhaustive or to limit the aspects to the precise form disclosed. Modifications and variations may be made in light of the above disclosure or may be acquired from practice of the aspects.

As used herein, the term "component" is intended to be broadly construed as hardware, firmware, and/or a combination of hardware and software. As used herein, a processor is implemented in hardware, firmware, and/or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the aspects. Thus, the operation and behavior of the systems and/or methods were described herein without reference to specific software code—it being understood that software and hardware can be designed to implement the systems and/or methods based, at least in part, on the description herein.

As used herein, satisfying a threshold may, depending on the context, refer to a value being greater than the threshold, greater than or equal to the threshold, less than the threshold, less than or equal to the threshold, equal to the threshold, not equal to the threshold, and/or the like.

Even though particular combinations of features are recited in the claims and/or disclosed in the specification, these combinations are not intended to limit the disclosure of various aspects. In fact, many of these features may be combined in ways not specifically recited in the claims and/or disclosed in the specification. Although each dependent claim listed below may directly depend on only one claim, the disclosure of various aspects includes each dependent claim in combination with every other claim in the claim set. A phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the terms "set" and "group" are intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," and/or the like are intended to be open-ended terms. Further, the phrase "based at least in part on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   receiving, from a vision sensor of a user device, first image data associated with a first set of images;
   processing a first subset of pixels of an image of the first set of images to determine whether an eye moved relative to a previous image of the first set of images;
   processing, based on processing the first subset of pixels, a second subset of pixels of the image of the first set of images to determine whether the eye moved relative to the previous image of the first set of images, wherein the second subset of pixels does not include a pixel of the first subset of pixels;
   determining, using an image processing model, that the first set of images depict a first type of eye activity of the eye based on processing the second subset of pixels;
   causing, based at least in part on determining that the first set of images depict the first type of eye activity, a power level, of a camera of the user device, to be reduced;
   receiving, from the vision sensor, second image data associated with a second set of images;
   determining, using the image processing model, that the second set of images depict a second type of eye activity of the eye; and
   causing, based at least in part on determining that the second set of images depict the second type of eye activity, the power level of the camera to be increased.

2. The method of claim 1, wherein the first type of eye activity corresponds to saccades motion of the eye.

3. The method of claim 1, wherein the first type of eye activity corresponds to eye activity that does not permit the eye to anatomically interpret optics and the second type of eye activity corresponds to eye activity that permits the eye to anatomically interpret optics.

4. The method of claim 1, wherein at least one of:
   the first set of images are associated with a larger pixel count than the second set of images; or
   the first set of images are a higher resolution than the second set of images.

5. The method of claim 1, wherein the vision sensor comprises a low-power sensor that facilitates an always-on motion detection mode to detect at least one of:
   the first type of eye activity, or
   the second type of eye activity.

6. The method of claim 5, wherein the always-on motion detection mode enables the vision sensor to record a sliding window of images corresponding to the second set of images.

7. The method of claim 1, wherein determining that the first set of images depict the first type of eye activity comprises:
   determining, based at least in part on the second subset of pixels having a different value than corresponding pixels of the previous image, that the eye moved in association with the first type of eye activity; and
   determining, based at least in part on determining that the eye moved in association with the first type of eye activity, that the first set of images depict the first type of eye activity.

8. The method of claim 1, wherein the image processing model is configured to detect the first type of eye activity based at least in part on the eye changing a gaze direction and the second type of eye activity based at least in part on the gaze direction of the eye remaining fixed for a threshold time period.

9. The method of claim 1, wherein the camera comprises a high-resolution camera and the vision sensor comprises a low-resolution camera.

10. The method of claim 1, wherein the vision sensor is configured to use less power than the camera.

11. The method of claim 1, wherein the vision sensor comprises at least one of:
    the camera in a low-power mode, or
    the camera in a low-resolution mode.

12. The method of claim 1, wherein the camera is configured to capture a third set of images for tracking eye gaze,
    wherein a virtual reality rendering or an augmented reality rendering is presented on a display of the user device based at least in part on the tracked eye gaze.

13. The method of claim 1, further comprising:
    causing the camera to capture a third set of images;
    processing the third set of images to track an eye gaze of the eye; and
    rendering, via a display of a user interface, graphics based at least in part on the eye gaze.

14. A device, comprising:
    one or more memories; and
    one or more processors, communicatively coupled to the one or more memories, configured to:
      receive, from a vision sensor, first image data associated with a first set of images;
      process a first subset of pixels of an image of the first set of images to determine whether an eye moved relative to a previous image of the first set of images;
      process, based on a processing of the first subset of pixels, a second subset of pixels of the image of the first set of images to determine whether the eye moved relative to the previous image of the first set of images, wherein the second subset of pixels does not include a pixel of the first subset of pixels;
      determine, using an image processing model, that the first set of images depict a first type of eye activity of the eye based on a processing of the second subset of pixels;

cause, based at least in part on determining that the first set of images depict the first type of eye activity, a power level, of a camera, to be reduced;
receive, from the vision sensor, second image data associated with a second set of images;
determine, using the image processing model, that the second set of images depict a second type of eye activity of the eye; and
cause, based at least in part on determining that the second set of images depict the second type of eye activity, the power level of the camera to be increased.

15. The device of claim 14, wherein the first set of images are a higher resolution than the second set of images.

16. The device of claim 14, wherein the camera comprises a high-resolution camera and the vision sensor comprises a low-resolution camera.

17. The device of claim 14, wherein the vision sensor is configured to use less power than the camera.

18. The device of claim 14, wherein the vision sensor comprises at least one of:
the camera in a low-power mode, or
the camera in a low-resolution mode.

19. The device of claim 14, wherein the first type of eye activity corresponds to saccades motion of the eye.

20. The device of claim 14, wherein the first type of eye activity corresponds to eye activity that does not permit the eye to anatomically interpret optics.

21. The device of claim 20, wherein the second type of eye activity corresponds to eye activity that permits the eye to anatomically interpret optics.

22. The device of claim 14, wherein the vision sensor comprises a low-power sensor that facilitates an always-on motion detection mode to detect at least one of:
the first type of eye activity, or
the second type of eye activity.

23. The device of claim 14, wherein the one or more processors are further configured to:
cause the camera to capture a third set of images;
process the third set of images to track an eye gaze of the eye; and
render, via a display of a user interface, graphics based at least in part on the eye gaze.

24. A non-transitory computer-readable medium storing a set of instructions, the set of instructions comprising:
one or more instructions that, when executed by one or more processors of a device, cause the device to:
receive, from a vision sensor, first image data associated with a first set of images;
process a first subset of pixels of an image of the first set of images to determine whether the eye moved relative to a previous image of the first set of images;
process, based on a processing of the first subset of pixels, a second subset of pixels of the image of the first set of images to determine whether the eye moved relative to the previous image of the first set of images, wherein the second subset of pixels does not include a pixel of the first subset of pixels;
determine, using an image processing model, that the first set of images depict a first type of eye activity of the eye based on a processing of the second subset of pixels;

cause, based at least in part on determining that the first set of images depict the first type of eye activity, a power level, of a camera, to be reduced;
receive, from the vision sensor, second image data associated with a second set of images;
determine, using the image processing model, that the second set of images depict a second type of eye activity of the eye; and
cause, based at least in part on determining that the second set of images depict the second type of eye activity, the power level of the camera to be increased.

25. The non-transitory computer-readable medium of claim 24, wherein the first set of images are a higher resolution than the second set of images.

26. The non-transitory computer-readable medium of claim 24, wherein the camera comprises a high-resolution camera and the vision sensor comprises a low-resolution camera.

27. The non-transitory computer-readable medium of claim 24, wherein the vision sensor is configured to use less power than the camera.

28. The non-transitory computer-readable medium of claim 24, wherein the vision sensor comprises at least one of:
the camera in a low-power mode, or
the camera in a low-resolution mode.

29. An apparatus, comprising:
means for receiving, from a vision sensor, first image data associated with a first set of images;
means for processing a first subset of pixels of an image of the first set of images to determine whether the eye moved relative to a previous image of the first set of images;
means for processing, based on a processing of the first subset of pixels, a second subset of pixels of the image of the first set of images to determine whether the eye moved relative to the previous image of the first set of images, wherein the second subset of pixels does not include a pixel of the first subset of pixels;
means for determining, using an image processing model, that the first set of images depict a first type of eye activity of the eye based on a processing of the second subset of pixels; and
means for causing, based at least in part on determining that the first set of images depict the first type of eye activity, a power level, of a camera, to be reduced.

30. The apparatus of claim 29, further comprising:
means for receiving, from the vision sensor, second image data associated with a second set of images;
means for determining, using the image processing model, that the second set of images depict a second type of eye activity of the eye; and
means for causing, based at least in part on determining that the second set of images depict the second type of eye activity, the power level of the camera to be increased.

* * * * *